US 7,111,493 B2

(12) United States Patent
Stull et al.

(10) Patent No.: US 7,111,493 B2
(45) Date of Patent: Sep. 26, 2006

(54) COMBUSTIBLE GAS DETECTION SYSTEM

(75) Inventors: Jeffrey Stull, Burlington, CT (US); Justin Baltrucki, Marlborough, CT (US); Andrzej Stanek, Meriden, CT (US); Edward Demarest, Bristol, CT (US); John Koopman, Colchester, CT (US); Daniel Rabbett, Ellington, CT (US)

(73) Assignee: Proton Energy Systems, Inc., Wallingford, CT (US)

( * ) Notice: Subject to any disclaimer, the term of this patent is extended or adjusted under 35 U.S.C. 154(b) by 94 days.

(21) Appl. No.: 10/707,324

(22) Filed: Dec. 5, 2003

(65) Prior Publication Data

US 2005/0000270 A1   Jan. 6, 2005

Related U.S. Application Data

(63) Continuation-in-part of application No. 10/065,862, filed on Nov. 26, 2002.

(51) Int. Cl.
*G01N 33/22* (2006.01)
(52) U.S. Cl. .................................... 73/23.31
(58) Field of Classification Search ............... 73/23.31
See application file for complete search history.

(56) References Cited

U.S. PATENT DOCUMENTS

| 4,271,474 | A | 6/1981 | Belanger et al. ............ 364/500 |
| 4,565,086 | A * | 1/1986 | Orr, Jr. ...................... 73/19.09 |
| 5,055,690 | A | 10/1991 | Bonne |
| 5,334,295 | A | 8/1994 | Gallagher et al. .......... 204/153 |
| 5,401,470 | A | 3/1995 | Poll |
| 5,690,797 | A | 11/1997 | Harada et al. |
| 5,707,148 | A | 1/1998 | Visser et al. |
| 6,096,178 | A | 8/2000 | Amirav et al. |
| 6,251,243 | B1 | 6/2001 | Lindsay ...................... 204/400 |
| 6,428,684 | B1 | 8/2002 | Warburton .................. 205/775 |
| 6,442,994 | B1 | 9/2002 | Slater |
| 6,454,923 | B1 | 9/2002 | Dodgson et al. ............ 204/415 |
| 6,468,412 | B1 * | 10/2002 | Bryan et al. ................. 204/242 |
| 6,475,651 | B1 | 11/2002 | Wilkinson et al. |
| 6,604,405 | B1 | 8/2003 | Whynall et al. |
| 6,739,177 | B1 * | 5/2004 | Sato et al. ................. 73/23.31 |
| 2002/0110713 | A1 | 8/2002 | Reindl et al. ................. 429/22 |
| 2004/0099045 | A1* | 5/2004 | Demarest et al. ............ 73/23.2 |
| 2006/0118428 | A1* | 6/2006 | Baltrucki et al. ........... 205/637 |

FOREIGN PATENT DOCUMENTS

WO   WO-99/17110 A1   4/1999

* cited by examiner

*Primary Examiner*—Hezron Williams
*Assistant Examiner*—John Fitzgerald
(74) *Attorney, Agent, or Firm*—Dave S. Christensen

(57) ABSTRACT

A system is provided for monitoring the levels of combustible gas in a gas stream. The system includes means for controlling the relative humidity of the gas stream and maintain a humidity level in the performance range of combustible gas sensors. A number of methods are illustrated for achieving the humidity control including secondary phase separations and the adjusting of the gas stream temperature.

2 Claims, 6 Drawing Sheets

COMBUSTIBLE GAS DETECTION SYSTEM

CROSS REFERENCE TO RELATED APPLICATIONS

The present application is a continuation in part of patent application Ser. No. 10/065,862 filed on Nov. 26, 2002.

FIELD OF THE INVENTION

This disclosure relates generally to the detection of combustible gases, and especially relates to the detection of hydrogen in a vent gas stream.

BACKGROUND OF THE INVENTION

Hydrogen gas is used and produced in many applications. Since the amount of hydrogen in a gas stream produced by a given process may be an indicator of system efficiency, the systems typically utilize sensors, such as combustible gas sensors to determine the level of hydrogen. An example of a prior art system having an arrangement for monitoring combustible gas is shown in FIG. 1A. The electrochemical system 12 receives water from an external source 14 and passes it through a deionizing bed 16. Once the water has been properly conditioned, it is supplied to an electrochemical cell 18 which disassociates the water into hydrogen and oxygen gas.

One example of an electrochemical cell 18 is a proton exchange membrane electrolysis cell which can function as a hydrogen generator by electrolytically decomposing water to produce hydrogen and oxygen gas, and can function as a fuel cell by electrochemically reacting hydrogen with oxygen to generate electricity. Referring to FIG. 1B, which is a partial section of a typical anode feed electrolysis cell 100, conditioned water 102 is fed into cell 100 on the side of an oxygen electrode (anode) 116 to form oxygen gas 104, electrons, and hydrogen ions (protons) 106. The reaction is facilitated by the positive terminal of a power source 120 electrically connected to anode 116 and the negative terminal of power source 120 connected to a hydrogen electrode (cathode) 114. The oxygen gas 103 and a portion of the process water 108 exit cell 100, while protons 106 and water 110 migrate across a proton exchange membrane 118 to cathode 114. At cathode 114, hydrogen gas 112 is formed and removed. Water is also removed from cathode 114.

A typical fuel cell uses the same general configuration as is shown in FIG. 1B. Hydrogen gas is introduced to the hydrogen electrode (the anode in fuel cells), while oxygen, or an oxygen-containing gas such as air, is introduced to the oxygen electrode (the cathode in fuel cells). Water can also be introduced with the feed gas. The hydrogen gas for fuel cell operation can originate from a pure hydrogen source, hydrocarbon, methanol, or any other hydrogen source that supplies hydrogen at a purity suitable for fuel cell operation (i.e., a purity that does not poison the catalyst or interfere with cell operation). Hydrogen gas electrochemically reacts at the anode to produce protons and electrons, wherein the electrons flow from the anode through an electrically connected external load, and the protons migrate through the membrane to the cathode. At the cathode, the protons and electrons react with oxygen to form water, which additionally includes any feed water that is dragged through the membrane to the cathode. The electrical potential across the anode and cathode can be exploited to power an external load.

In other embodiments, one or more electrochemical cells can be used within a system to both electrolyze water to produce hydrogen and oxygen, and to produce electricity by converting hydrogen and oxygen back into water as needed. Such systems are commonly referred to as regenerative fuel cell systems.

After the electrochemical cell 18 disassociates the water, oxygen and hydrogen gas exit the cell 18 through conduits 20 and 22 respectively. As mentioned herein above, in addition to the gas products, water entrained in the gases exits with the oxygen and hydrogen. The hydrogen conduit 22 typically connects with a hydrogen phase separator 24 which extracts most of the water from the gas, with the water exiting the phase separator 24 through a valving arrangement which recycles the water back into the electrochemical cell water feed conduit. Depending on the needs of the application, additional water may be removed from the hydrogen gas by passing through an optional desiccant gas dryer 26 before exiting the process for use in the application.

The oxygen gas stream 20 also enters into a phase separator 28 with a majority of the water separating from the gas stream and dropping to the bottom of the separator 28. As with the hydrogen separator 24 this water is removed and recycled into the electrochemical cell water feed conduit. The separated hydrogen gas exits the phase separator 28 via a conduit 32 to exit the process. Since it is desirable to monitor for the presence of hydrogen gas in the oxygen gas stream through an orifice 40 to a combustible gas sensor 36. A gas dryer 38, such as a NAFION tube dryer, is usually placed in line between the phase separator 28 and the sensor 36 to remove water still entrained in the gas. Unfortunately, since the gas stream can still have a relative humidity greater than 95%. This high relative humidity results in lower monitoring performance than is desired.

Accordingly, what is needed in the art is a system for monitoring combustible gas levels in a gas stream that reduces or eliminates the effects of relative humidity on the combustible gas sensor.

SUMMARY OF INVENTION

A system for monitoring combustible gas includes a phase separator having a first outlet, a conduit having an inlet connected to said phase separator and an exhaust outlet, and a combustible gas sensor adjacent said exhaust outlet and connected to said conduit. The combustible gas sensor is generally mounted perpendicular to either the gas stream exhaust or the gas inlet exhaust. The conduit is generally made of a metal composition or from a conductive polymer.

An alternate embodiment of the system for monitoring combustible gas includes a bracket having a main body and a first flange on one end of said body and a second flange on an end of said body opposite said first flange. A housing is mounted to the bracket, and the housing has an opening to receive a gas stream. A combustible gas sensor mounted to the first flange.

A system for generating hydrogen gas includes an electrochemical cell stack having a phase separator fluidly coupled to the electrochemical stack for receiving a water gas mixture. A vent conduit fluidly connected and extending vertically from the top of the phase separator, and a combustible gas sensor coupled to the vent conduit

BRIEF DESCRIPTION OF DRAWINGS

Referring now to the drawings, which are meant to be exemplary and not limiting, and wherein like elements are numbered alike.

DETAILED DESCRIPTION

Hydrogen gas is a versatile material having many uses in industrial and energy application ranging from the production of ammonia, to power vehicles being propelled into space. Since the hydrogen molecule is one of the smallest known particles, containing and controlling leaks of hydrogen gas is very difficult. Monitoring of these leaks is important as it is typically an indicator of performance degradation and or component wear. Typically, prior art systems have used combustible gas sensors to monitor levels of combustible gas in the system. When unacceptable levels of hydrogen are detected in the system, the system is either shut down, or the operator is alerted that preventative maintenance is required.

Commercial combustible gas sensors typically use a technology referred to as a "catalytic bead" type sensor, such as the Detcon, Inc. Model FP-524C. These sensors monitor the percentage of lower explosive limit ("LEL") of combustible gas in a product gas stream. This LEL measurement represents the percentage of a combustible gas, such as hydrogen, propane, natural gas, in a given volume of air. One limitation of catalytic bead sensors is their sensitivity to moisture in the gas they are monitoring. Once the gas reaches 95% relative humidity, the ability of the sensor to detect combustible gas deteriorates resulting in less than desirable life and reliability. Many hydrogen applications, including but not limited to electrochemical cells, electrolyzers, fuel cells and methane steam reformers, also utilize water in their processes which tends to effect the relative humidity of the product gas stream being monitored. It should be appreciated that while the examples described herein typically refer to electrochemical systems such as electrolyzers or fuel cells, the present invention can be equally applied in any application where a combustible gas needs to be monitored.

Figure 1A:
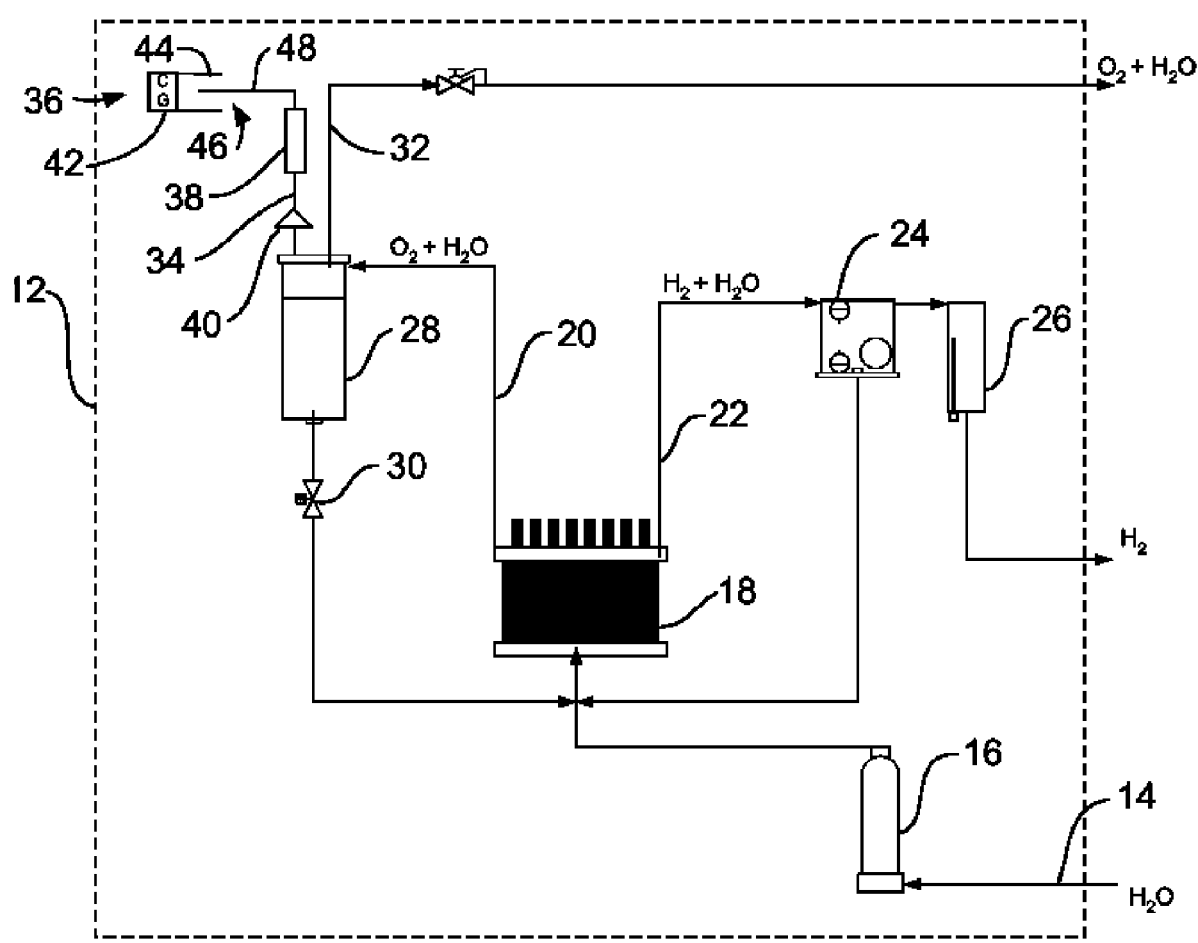
FIG. 1A is a schematic drawing of an electrochemical system having a combustible gas detection system used in the prior art.
Figure 1B:
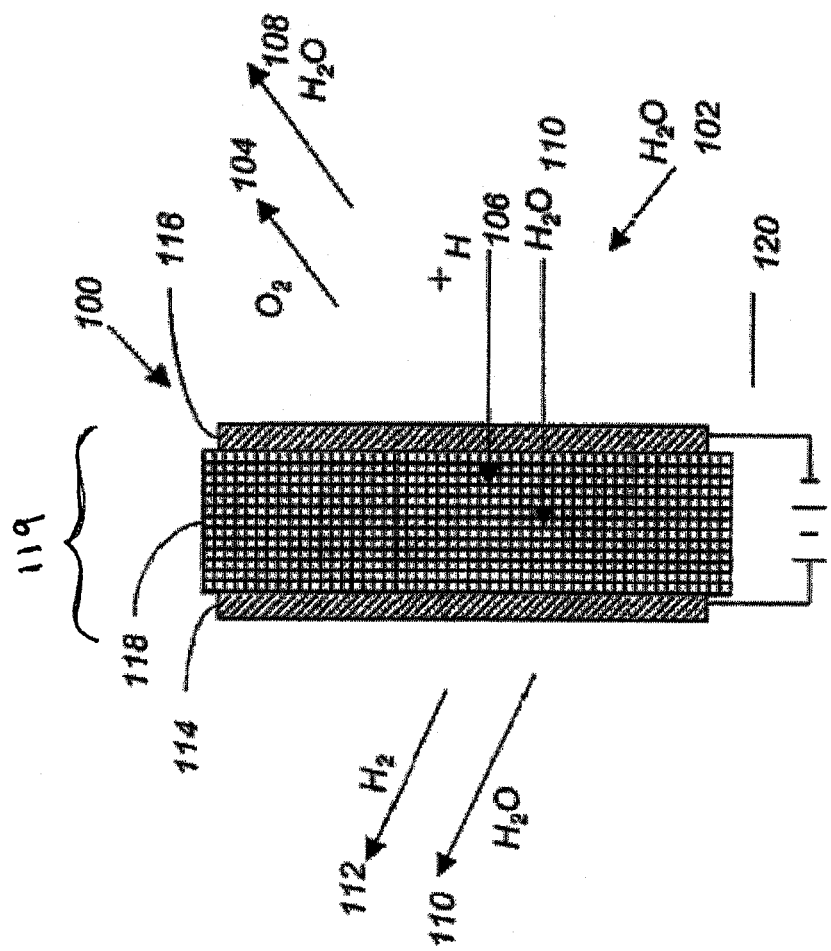
FIG. 1B is a schematic diagram of a partial prior art electrochemical cell showing an electrochemical reaction.

Referring to FIGS. 1A and 1B, and electrochemical system 12 of the present invention is shown. Electrochemical cells 18 typically include one or more individual cells arranged in a stack, with the working fluids directed through the cells within the stack structure. The cells within the stack are sequentially arranged, each including a cathode, proton exchange membrane, and an anode (hereinafter "membrane electrode assembly", or "MEA" 119) as shown in FIG. 1B. Each cell typically further comprises a first flow field in fluid communication with the cathode and a second flow field in fluid communication with the anode. The MEA 119 may be supported on either or both sides by screen packs or bipolar plates disposed within the flow fields, and which may be configured to facilitate membrane hydration and/or fluid movement to and from the MEA 119.

Membrane 118 comprises electrolytes that are preferably solids or gels under the operating conditions of the electrochemical cell. Useful materials include, for example, proton conducting ionomers and ion exchange resins. Useful proton conducting ionomers include complexes comprising an alkali metal salt, alkali earth metal salt, a protonic acid, a protonic acid salt or mixtures comprising one or more of the foregoing complexes. Counter-ions useful in the above salts include halogen ion, perchloric ion, thiocyanate ion, trifluoromethane sulfonic ion, borofuoric ion, and the like. Representative examples of such salts include, but are not limited to, lithium fluoride, sodium iodide, lithium iodide, lithium perchlorate, sodium thiocyanate, lithium trifluoromethane sulfonate, lithium borofluoride, lithium hexafluorophosphate, phosphoric acid, sulfuric acid, trifluoromethane sulfonic acid, and the like. The alkali metal salt, alkali earth metal salt, protonic acid, or protonic acid salt can be complexed with one or more polar polymers such as a polyether, polyester, or polyimide, or with a network or cross-linked polymer containing the above polar polymer as a segment. Useful polyethers include polyoxyalkylenes, such as polyethylene glycol, polyethylene glycol monoether, and polyethylene glycol diether; copolymers of at least one of these polyethers, such as poly(oxyethylene-co-oxypropylene) glycol, poly(oxyethylene-co-oxypropylene) glycol monoether, and poly(oxyethylene-co-oxypropylene) glycol diether; condensation products of ethylenediamine with the above polyoxyalkylenesl; and esters, such as phosphoric acid esters, aliphatic carboxylic acid esters or aromatic carboxylic acid esters of the above polyoxyalkylenes. Copolymers of, e.g., polyethylene glycol monoethyl ether with methacrylic acid exhibit sufficient ionic conductivity to be useful.

Ion-exchange resins useful as proton conducting materials include hydrocarbon and fluorocarbon-type resins. Hydrocarbon-type ion-exchange resins include phenolic resins, condensation resins such as phenol-formaldehyde, polystyrene, styrene-divinyl benzene copolymers, styrene-butadiene copolymers, styrene, styrene-divinylbenzene-vinylchloride terpolymers, and the like, that can be imbued with cation-exchange ability by sulfonation, or can be imbued with anion-exchange ability by chloromethylation followed by conversion to the corresponding quaternary-amine.

Fluorocarbon-type ion-exchange resins can include, for example, hydrates of tetrafluoroethylene-perfluorosulfonyl ethoxyvinyl ether or tetrafluoroethylene-hydroxylated (perfluorovinylether) copolymers and the like. When oxidation and or acid resist is desirable, for instance, at the cathode of a fuel cell, fluorocarbon-type resins having sulfonic, carboxylic and/or phosphoric acid functionality are preferred. Fluorocarbon-type resins typically exhibit excellent resistance to oxidation by halogen, strong acids, and bases. One family of fluorocarbon-type resins having sulfonic acid group functionality is NAFION™resins (commercially available from E.I. du Pont de Nemours and Company, Wilmington, Del.).

Electrodes 114 and 116 comprise catalyst suitable for performing the needed electrochemical reaction (i.e. electrolyzing water to produce hydrogen and oxygen). Suitable electrodes comprise, but are not limited to, platinum, palladium, rhodium, carbon, gold, tantalum, tungsten, ruthenium, iridium, osmium, and the like, as well as alloys and combinations comprising one or more of the foregoing materials. Electrodes 114 and 116 can be formed on membrane 118, or may be layered adjacent to, but in contact with or in ionic communication with, membrane 118.

Flow field members (not shown) and support membrane 118, allow the passage of system fluids, and preferably are electrically conductive, and may be, for example, screen packs or bipolar plates. The screen packs include one or more layers of perforated sheets or a woven mesh formed from metal or strands. These screens typically comprise metals, for example, niobium, zirconium, tantalum, titanium, carbon steel, stainless steel, nickel, cobalt and the like, as well as alloys and combinations comprising one or more of the foregoing metals. Bipolar plates are commonly porous structures comprising fibrous carbon, or fibrous carbon impregnated with polytetrafluoroethylene or PTFE (commercially available under the trade name TEFLON® from E.I. du Pont de Nemours and Company).

After hydrogen and oxygen have been disassociated from the water, the hydrogen exits the electrochemical cell 18 as described herein above via the separator 24 and an optional dryer 26. The oxygen gas and excess process water exit the electrochemical cell through a conduit 20 which carries the oxygen and water into a phase separator 50 and exits the system through exhaust outlet 54. It should be noted that while the phase separator 50 removes water from the gas stream, the oxygen gas typically exits the separator 50 in a saturated condition with a relative humidity in excess of 95%.

Figure 2:
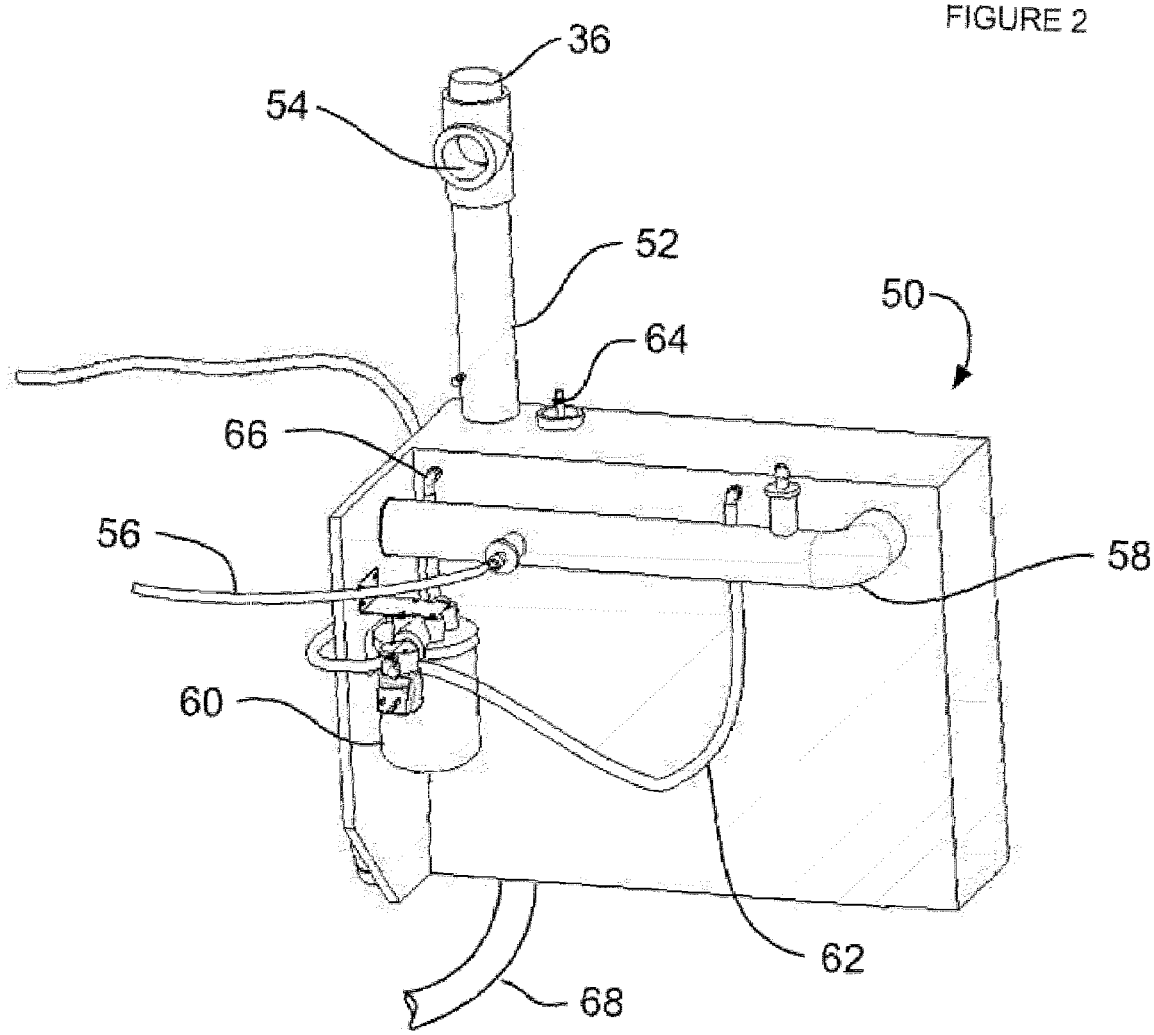
FIG. 2 is an illustration of an exemplary embodiment of a oxygen-water phase separator having a combustable gas detector incorporated into the gas vent stream.
Figure 5:
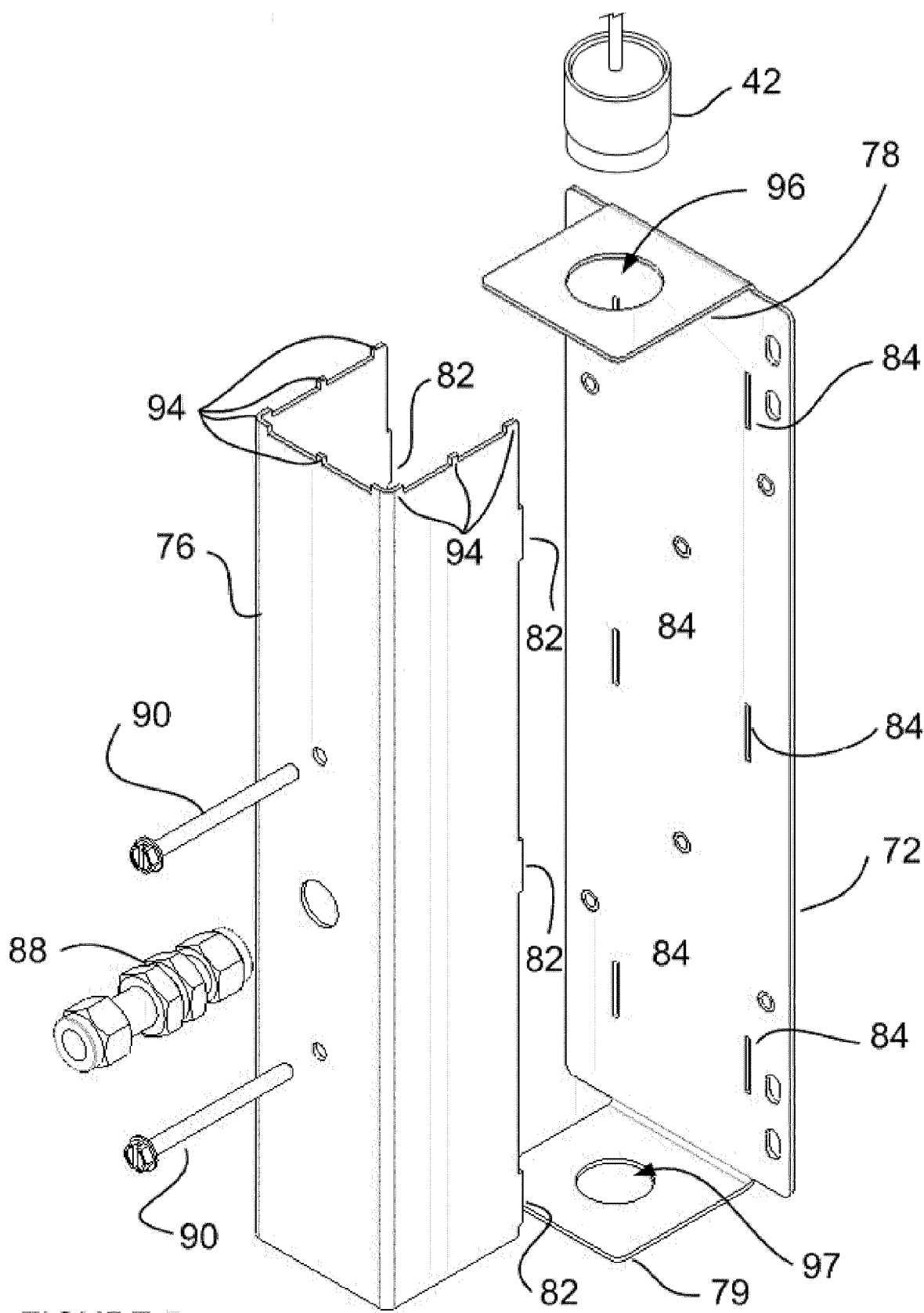
FIG. 5 is an exploded view of the assembly of the combustible gas sensor arrangement of FIG. 3.

Since high relative humidity has undesirable effects, the present invention addresses these issues by either controlling the temperature of the gas stream or by controlling the pressure of the gas stream. Referring to FIGS. 2 5, two different types of combustible gas sensor arrangements are shown. As will be described in more detail herein, the arrangement of the gas sensor in combination with other components reduce the relative humidity of the sampled gas to increase the performance of combustible gas measurements.

The combustible gas ("CG") sensor arrangement utilized by the prior art is shown in FIG. 1A. In this arrangement, the CG sensor device 36 includes a CG sensor 42 and a housing 44. The housing 44 is typically tubular in shape and attaches to the sensor 42 by any convenient means such as a thread (not shown). The CG sensor 42 also includes a sensing face 43 which detects the levels of combustible gas, this face 43 is located opposite a housing open end 46. A gas sample tube 48 is inserted into the open end 46. During operation, the saturated gas stream 49 exits the sample tube 48 and mixes with the air in the housing allowing some drying of the saturated gas.

An exemplary embodiment of the CG sensor of the present invention is shown in FIG. 2. In this embodiment, the CG sensor 36 is mounted to one end of a vent conduit 52 adjacent a vent exhaust 54. The conduit 52 is vertically connected to above a water-gas phase separator 50. The separator 50 is a large container which receives water from an upstream process such as an electrochemical cell 18 through tubes 56, 58. The separator may also utilize other components such as filters 60, water lines 62, level sensors 64, and overflow drain 66.

In operation, the separator 50 receives the process water which may contain entrained gases, including oxygen and possibly combustible gas, from tube 58. As the water mixture enters the separator 50 it experiences a slight pressure drop causing some of the water entranced in the stream to condense and drop to the bottom of the phase separator. The separated water exits via a conduit 68 to be either recycled back into the process or is otherwise disposed of. The liberated gases, exit through conduit 52 and exit the system through exhaust outlet 54. As the gas vertically ascends conduit 52, additional water is separated from the gas stream through condensation on the side walls of conduit 52. In the preferred embodiment, the conduit 52 is made from a metal such as stainless steel to enhance the condensation of water out of the gas. By knowing the operating conditions of the process and the temperature of the environment, the conduit 52 may be sized appropriately to dry the gas to desired relative humidity level to allow the CG sensor 36 to function as desired. A conductive metallic conduit 52 also provides additional benefit in providing an electrical ground for the sensor 36. It should be noted that the electrical grounding provides a further benefit of eliminating a possible voltage potential between the sensor and the conduit. By eliminating the voltage potential, the possibility of an electrical arc forming between the sensor 36 and the conduit 52 is also eliminated, which is advantageous when operating in an environment which may contain combustible gases. Alternatively to the metallic conduit, a conductive polymer could also be used to achieve the appropriate grounding. The CG sensor 36 being positioned adjacent and perpendicular to the exhaust port 54 allows the monitoring of the gas to ensure that any combustible gases present are maintained at appropriate levels.

Figure 3:
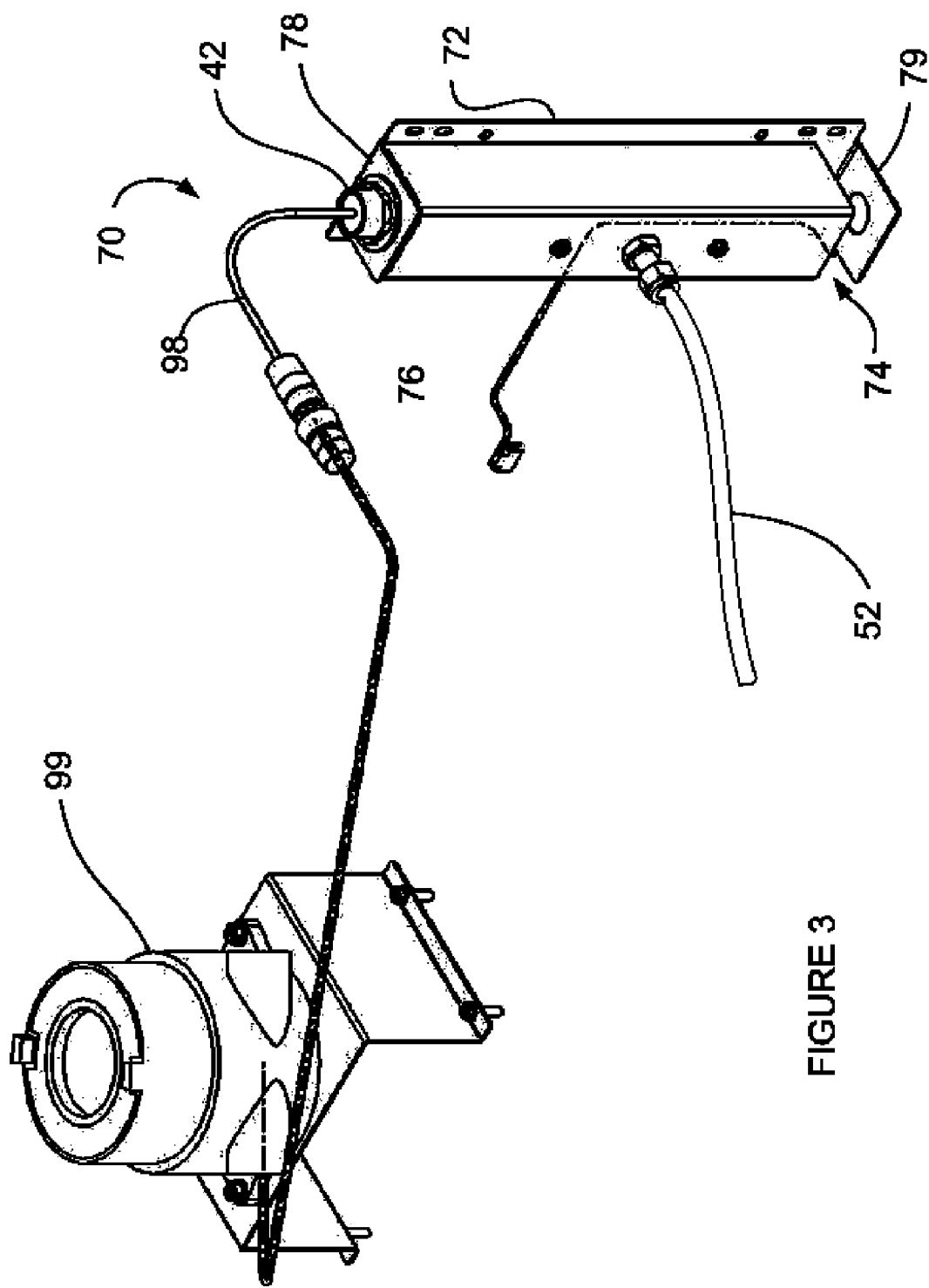
FIG. 3 is an illustration of an alternate embodiment of a combustible gas sensor arrangement.
Figure 4:
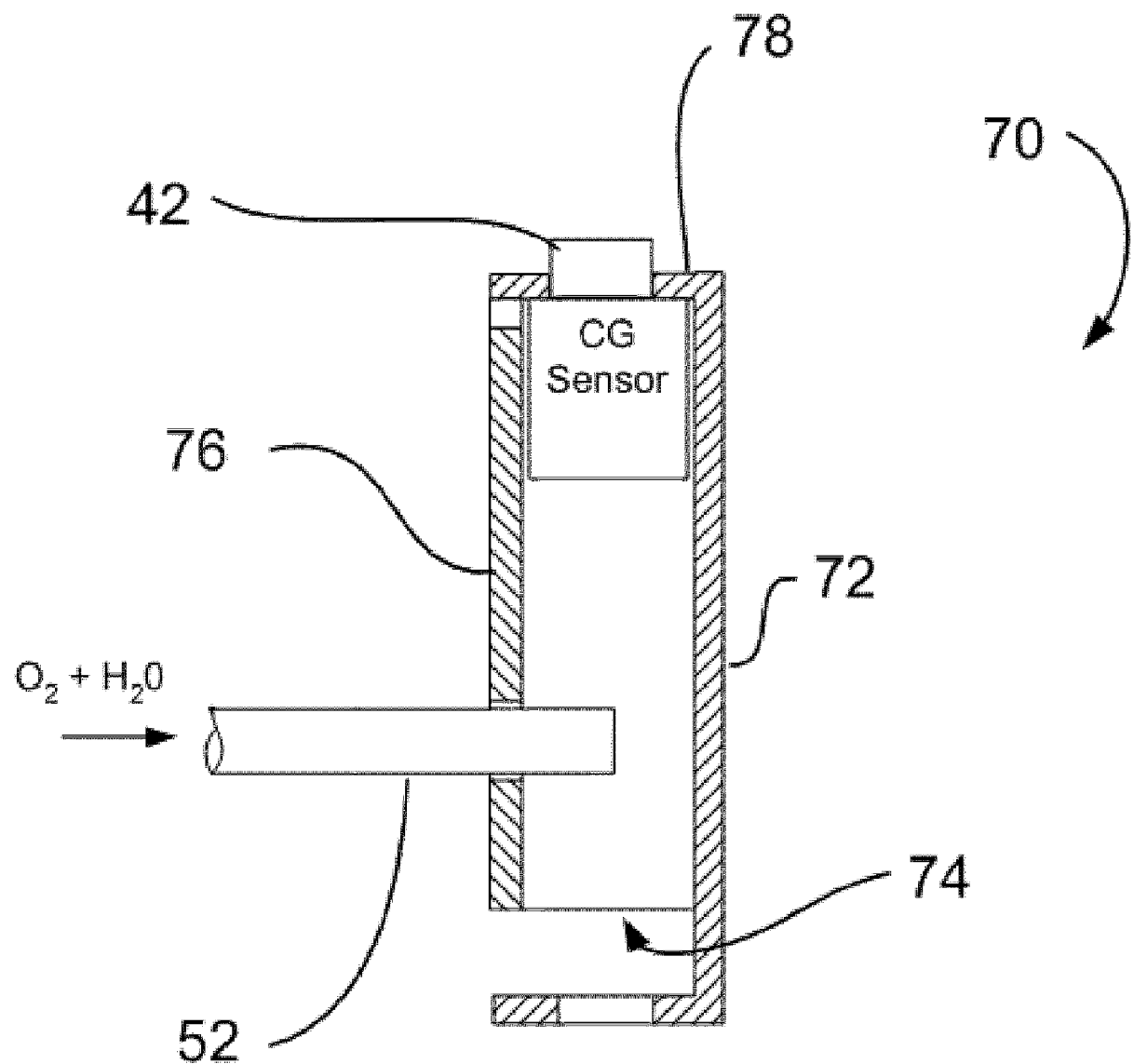
FIG. 4 is a simplified cross-section view of the of the combustible gas sensor arrangement of FIG. 3.

An alternate embodiment of combustible gas sensing arrangement is shown in FIGS. 3–5. This embodiment comprises a sensor assembly 70 having a housing 76 secured to a bracket 72 by a pair of fasteners 90 which thread into corresponding holes 92. A set of tabs 82 in housing 76 are sized and positioned to fit into corresponding slots 84 in the bracket 72. To connect the vent conduit 52 to the assembly 70 a coupling 88 secures the conduit 52 to a hole 86 in the housing 76. The housing 76 further includes projections 94 on one end which provide for venting of the enclosed space created by the assembly. To provide for flexibility in manufacturing of the assembly 70, the bracket 72 includes a first flange 78 and second flange 79 for the mounting of the CG sensor 42. CG sensors 42 from different manufacturers may be of different sizes. To accommodate this variation, the CG sensor mounting holes 96 and 97 are of different sizes. To switch from one CG sensor manufacturer to another simply requires the bracket 72 to be rotated 180°, orienting the flange 79 on top and mounting the CG sensor 42 to the flange 79. A cable 98 connected to CG sensor 42 carries signals generated by the sensor 42 to a monitoring unit 99.

In this embodiment, which may be preferred in applications where a vertical conduit is undesirable, the conduit 52 is connected to a sensor assembly 70 by coupling 88. As best shown in FIG. 4, the oxygen gas stream enters the assembly 70 through a housing 76 and impinges on bracket 72. As with the phase separator 50, as the stream enters the assembly 70, it experiences a further pressure drop which causes the relative humidity to less than 95%. The dried gas and any water exit through the open bottom portion 74. Due to the mixing of the gas stream within the assembly 70 when the stream contacts the bracket 72, the CG sensor 36 is able to monitor for levels of combustible gas. By arranging the sensor vertically above the entrance of the gas stream, the sensor 42 can be protected from liquids in the stream and providing a drier gas for monitoring. Since combustible gases such as hydrogen are lighter than air, any hydrogen mixed with the oxygen gas stream will disperse vertically toward the CG sensor 42, to prevent the accumulation of combustible gases in the assembly 70 which would result in faulty measurements, a set of vent openings formed between the housing and the flange 78 by the projections 94 adjacent to the CG sensor 42.

It should be appreciated that the flanges 78, 79 for mounting the CG sensor 42 may alternatively be located on the housing 76. Additional advantages in calibration of the sensor 42 are achieved by positioning the flanges 78, 79 as shown in the preferred embodiment. CG sensors such as those which are described herein require a periodic calibration to ensure proper measurements. These calibration procedures typically involve using a canister of premixed combustible gas having a predetermined LEL and introducing the gas to the sensor. For accurate results to be achieved, the premixed gas must be introduced directly adjacent the sensor. To calibrate the system as shown in the preferred embodiment, the user simply needs to remove the housing 76 by removing bolts 90 without disturbing the CG sensor. The premixed gas can then be introduced to the sensor 42 without any physical hindrances to the procedure.

While preferred embodiments have been shown and described, various modifications and substitutions may be made thereto without departing from the spirit and scope of the invention. For example, while the embodiments shown referred specifically to an electrochemical system generating hydrogen, this invention would apply equally to any system where there is a potential for mixing hydrogen with air or oxygen including, but not limited to photolysis, fuel cells, steam methane reformers or hydrocarbon reformers. Accordingly, it is to be understood that the present invention has been described by way of illustrations and not limitation.

The invention claimed is:

1. A system for generating hydrogen gas comprising:
   an electrochemical cell stack;
   a phase separator fluidly coupled to said electrochemical stack for receiving a water gas mixture;
   a metallic vent conduit fluidly connected and extending vertically from the top of said phase separator; and,
   a combustible gas sensor coupled and electrically grounded to said vent conduit, wherein said vent conduit further comprises an exhaust outlet.

2. The system for generating hydrogen gas of claim 1 wherein said combustible gas sensor is positioned adjacent to said exhaust outlet.

* * * * *